(12) United States Patent
Malvankar et al.

(10) Patent No.: US 11,250,937 B2
(45) Date of Patent: Feb. 15, 2022

(54) SYSTEM AND METHOD TO SHARE AND UTILIZE HEALTHCARE DATA

(71) Applicant: INTERNATIONAL BUSINESS MACHINES CORPORATION, Armonk, NY (US)

(72) Inventors: Abhishek Malvankar, White Plains, NY (US); Saurabh Pujar, White Plains, NY (US); Edward A. Epstein, Putnam Valley, NY (US); Louis Degenaro, White Plains, NY (US); Burn Lewis, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 63 days.

(21) Appl. No.: 16/383,120

(22) Filed: Apr. 12, 2019

(65) Prior Publication Data
US 2020/0327969 A1    Oct. 15, 2020

(51) Int. Cl.
*G16H 15/00*    (2018.01)
*G06N 20/20*    (2019.01)
*H04L 9/06*    (2006.01)
*G16H 10/60*    (2018.01)

(52) U.S. Cl.
CPC .............. *G16H 15/00* (2018.01); *G06N 20/20* (2019.01); *G16H 10/60* (2018.01); *H04L 9/0637* (2013.01)

(58) Field of Classification Search
CPC .......... G16H 15/00; G16H 10/60; G06N 20/00
See application file for complete search history.

(56) References Cited

U.S. PATENT DOCUMENTS

| 10,116,913 | B2 | 10/2018 | Kim | |
| 10,327,697 | B1 * | 6/2019 | Stein | G06K 9/66 |
| 2015/0379424 | A1 | 12/2015 | Dirac et al. | |
| 2016/0148115 | A1 | 5/2016 | Sirosh et al. | |
| 2018/0018590 | A1 | 1/2018 | Szeto et al. | |
| 2018/0165588 | A1 | 6/2018 | Saxena et al. | |
| 2019/0371457 | A1 * | 12/2019 | Paffel | H04L 9/3242 |
| 2020/0013124 | A1 * | 1/2020 | Obee | G06N 20/00 |

(Continued)

OTHER PUBLICATIONS

Kuo, T., "ModelChain: Decentralized Privacy-Preserving Healthcare Predictive Modeling Framework on Private Blockchain Networks." (Submitted on Feb. 6, 2018), https://arxiv.org/abs/1802.01746., 13 pgs.

(Continued)

*Primary Examiner* — Sheetal R Paulson
(74) *Attorney, Agent, or Firm* — L. Jeffrey Kelly

(57) ABSTRACT

A computer-implemented method, system and computer program product for sharing and utilizing healthcare data, by: providing one or more computer-implemented machine learning models for analyzing the healthcare data; and recording transactions involving the machine learning models using a blockchain as a distributed ledger that is shared, replicated and synchronized. Healthcare data is also used to train the machine learning models. The healthcare data comprises research data or patient data such as Electronic Medical Records (EMRs). A smart contract that is a computer-implemented protocol is used to facilitate, verify or enforce negotiation of the transactions involving the machine learning models or healthcare data.

19 Claims, 4 Drawing Sheets

(56) References Cited

U.S. PATENT DOCUMENTS

2020/0098106 A1* 3/2020 Moriyasu ............... G06N 20/00

OTHER PUBLICATIONS

Wu, Y., "Grid Binary LOgistic REgression (GLORE): Building Shared Models without Sharing Data." Journal of the American Medical Informatics Association: JAMIA 19.5 (2012), pp. 758-764.

Jiang, W., "WebGLORE: A Web Service for Grid LOgistic REgression." Bioinformatics 29.24 (2013), pp. 3238-3240.

Lu, C., "WebDISCO: a web service for distributed cox model learning without patient-level data sharing." J. Am Med Inform Assoc. Nov. 2015; 22(6), pp. 1212-1219. doi: 10.1093/jamia/ocv083.

Peterson, K., "A Blockchain-Based Approach to Health Information Exchange Networks," 2016, ONC/NIST Use of Blockchain for Healthcare and Research Workshop, Gaithersburg, Maryland: ONC/NIST; 2016. [online] Available: https://www.healthit.gov/sites/default/files/12-55-blockchain-based-approach-final.pdf., pp. 1-10.

https://github.com/ibm-watson-iot/blockchain-samples/tree/master/docs, "Introduction to Hyperledger Smart Contracts for IoT Best Practices and Patterns", Accessed on Oct. 16, 2020, 16 pages.

https://hyperledger-fabric.readthedocs.io/en/v1.0.0-beta/FAQ/chaincode, "Chaincode (Smart Contracts and Digital Assets)", Accessed on Oct. 16, 2020, 2 pages.

https://link.springer.com/chapter/10.1007/978-3-319-59665-5_15?no-access=true, "Blockchain Based Access Control", SpringerLink, IFIP International Conference on Distributed Applications and Interoperable Systems, DAIS 2017, Conference paper, First Online: May 24, 2017, 5 pages.

Numerai, "The hardest data science tournament on the planet.", Build the world's open hedge fund by modeling the stock market, https://numer.ai/, Accessed on Oct. 16, 2020, 5 pages.

Yegulalp, "ONNX makes machine learning models portable, shareable", Microsoft and Facebook's machine learning model format aims to let devs choose frameworks freely and share trained models without hassle, Sep. 8, 2017, 4 pages.

Zhang et al., "Town Crier: An Authenticated Data Feed for Smart Contracts", CCS'16, Oct. 24-28, 2016, Vienna, Austria, © 2016 ACM, 13 pages.

* cited by examiner

SYSTEM AND METHOD TO SHARE AND UTILIZE HEALTHCARE DATA

BACKGROUND

Some organizations have healthcare data, but not the expertise to obtain insights from the healthcare data. Other organizations are service providers with the expertise to obtain insights from healthcare data, but do not have the healthcare data. Yet other organizations have both healthcare data and are service providers with the expertise to obtain insights from healthcare data.

Even if organizations have healthcare data and/or are service providers with the expertise to obtain insights from the healthcare data, it is difficult to obtain fair value for these assets. There is no easy way for owners of data owners and service providers to collaborate. Thus, there is need for improved methods and systems to encourage sharing of analysis and resources produced from healthcare data. The present invention satisfies this need.

SUMMARY

The invention provided herein has a number of embodiments useful, for example, in a computer-implemented method, system and computer program product, for sharing and utilizing healthcare data, by: providing one or more computer-implemented machine learning models for analyzing the healthcare data; and recording transactions involving the machine learning models using a blockchain as a distributed ledger that is shared, replicated and synchronized. Moreover, healthcare data is also used to train the machine learning models. The healthcare data may comprise research data or patient data.

The blockchain records access to and usage of the machine learning models and healthcare data. The blockchain also tracks dependencies among the machine learning models and healthcare data. In addition, the blockchain tracks services built upon the machine learning models and healthcare data.

The blockchain includes at least one uniform resource locator (URL) that provides access to the machine learning models and healthcare data that is delivered as a service. The blockchain also provides for selection among the machine learning models, wherein metadata is used to select among the machine learning models and healthcare data.

The blockchain ensures that access to the healthcare data is in compliance with regulatory requirements.

The blockchain also records transactions between owners of the machine learning models and healthcare data, for example, the blockchain may be used to transfer rights to use the machine learning models.

A smart contract that is a computer-implemented protocol is used to facilitate, verify or enforce negotiation of the transactions involving the machine learning models and healthcare data.

DRAWINGS

Referring now to the drawings in which like reference numbers represent corresponding parts throughout:

DETAILED DESCRIPTION

In the following description, reference is made to the accompanying drawings which form a part hereof, and in which is shown by way of illustration one or more specific embodiments in which the invention may be practiced. It is to be understood that other embodiments may be utilized and structural and functional changes may be made without departing from the scope of the present invention.

Overview

Figure 1:
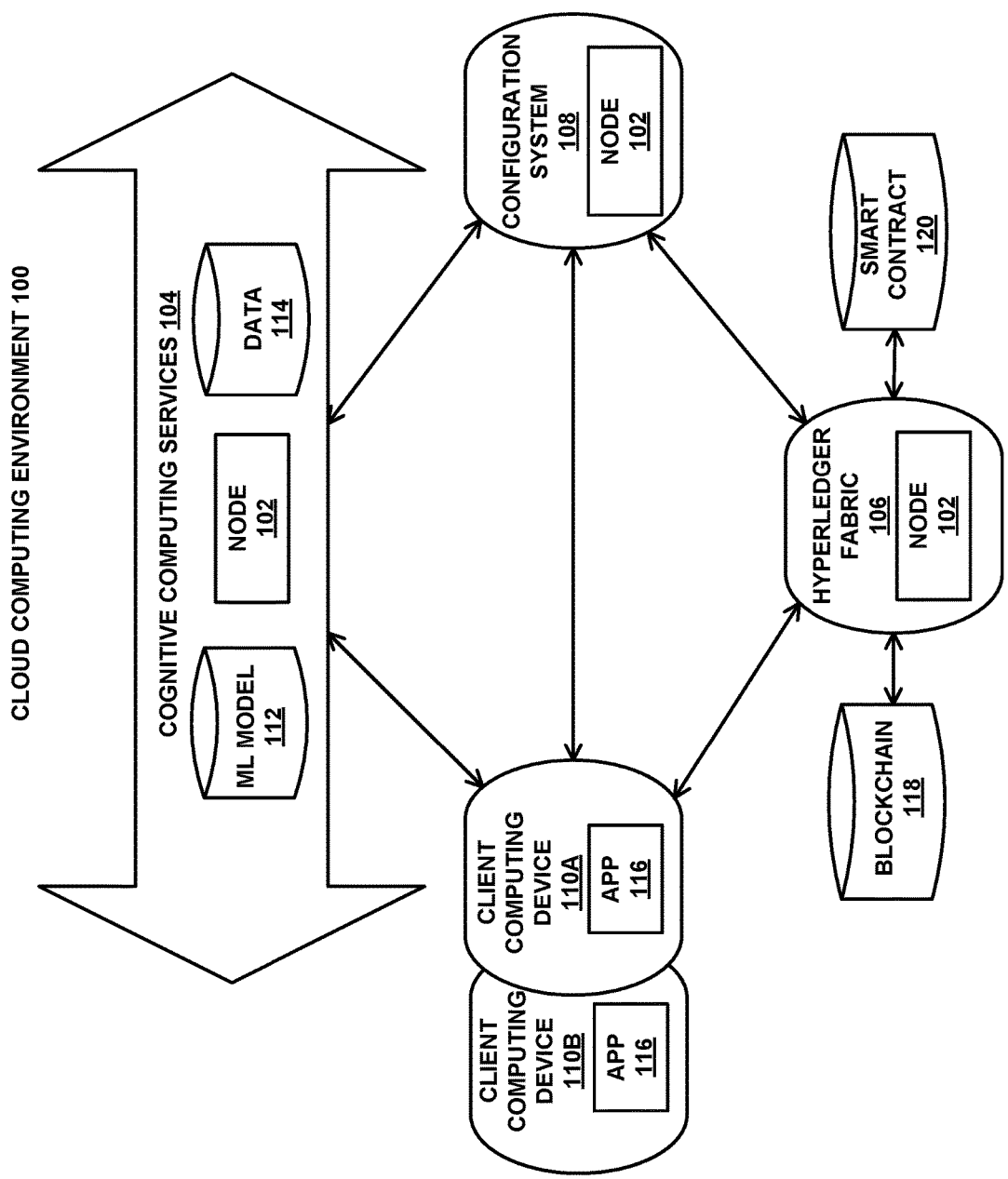
FIG. 1 illustrates an exemplary system for sharing and utilizing healthcare-derived resources according to an embodiment of the present invention.

FIG. 1 illustrates an exemplary system for sharing and utilizing healthcare-derived resources according to an embodiment of the present invention. A cloud computing environment 100 comprised of one or more nodes 102 used for implementing cognitive computing services 104 that use the healthcare-derived resources, a hyperledger fabric 106 that is a blockchain network used to track and audit transactions made using the healthcare-derived resources, and a configuration system 108 that configures information and data flow in the system. One or more client computing devices 110A, 110B operated by end-users interact with these components 104, 106, 108 to apply artificial intelligence (AI) techniques to obtain insights using the healthcare-derived resources, for example, using one or more computer-implemented machine learning (ML) models 112 to analyze healthcare data 114.

Cognitive Computing Services

Insights on healthcare-derived resources can be obtained by a variety of artificial intelligence techniques, including sophisticated techniques such as supervised or unsupervised machine learning. Machine learning is defined broadly as computer-implemented methods and systems for simulating intelligence by using data to tune algorithms.

In one embodiment of the present invention, the machine learning models 112 are trained using healthcare data 114, and the trained machine learning models 112 are then used for analyzing other healthcare data 114. In both instances, the healthcare data 114 comprises research data and/or patient data from electronic medical records (EMRs). The functionality for training and using the machine learning models 112 is provided by the cognitive computing services 104.

In one embodiment, the cognitive computing services 104 are implemented using the Watson™ services offered by IBM Corporation, the assignee of the present invention. However, other machine learning services could also be used.

The Watson™ services comprise a set of services that can be used to create, store, deploy and use machine learning models 112. Specifically, the Watson™ services provide an infrastructure for performing an analysis of data 114 using machine learning models 112, in order to recognize patterns in that data 114 and generate predictions based on those patterns.

The key services provided by the Watson™ services include:
Repository service—Stores the models 112 that are created so that they can be retrieved to create deployments.
Deployment service—Deploys models 112 so that they can be used for predictions.

Scoring service—Uses the deployed models 112 to perform data analysis and generate predictions from patterns found in the data.

The Watson™ services also provide application programming interfaces (APIs) that enable applications to search, explore, and administer collections of machine learning models 112. These APIs allow applications to use hypertext transport protocol (HTTP) requests to post data (create and update), read data (such as running queries), delete data, and return data (responses to queries). Alternative mechanisms may be used as well.

In the present invention, one or more machine learning models 112 trained by healthcare data 114 collected from various sources, are used by the cognitive computing services 104 for formulation of any useful insights from healthcare data 114. For example, to train a machine learning model 112, research data 114 may be imported into the cognitive computing services 104 and the machine learning model 112 could then be consumed by other cognitive computing services 104, which is a HIPAA-compliant system, to make classifications or predictions on patient data 114.

A user interface (UI) to access various exposed machine learning models 112 is packaged in an application (app) 116, which is delivered to the client computing devices 110A, 110B for execution, for example, in a web browser. The machine learning models 112 are exposed as an insights service provided by the cognitive computing services 104. A uniform resource locator (URL) for the machine learning model 112 used by the insights service is maintained by the hyperledger fabric 106, which supplies the URL to the app 116 when access is granted to the machine learning model 112 plugged into one of the cognitive computing services 104.

Thereafter, the insights service provided by the cognitive computing services 104 is invoked by the app 116 on the client computing devices 110A, 110B operated by an end-user, wherein the app 116 supplies patient data 114 to the cognitive computing services 104 for use with the machine learning model 112. The machine learning model 112 analyzes the data 114 and generates a response thereto, which is returned by the insights service to the app 116.

The Watson™ services are capable of analyzing high volumes of data 114, recognizing patterns in the data 114, understanding complex questions posed in natural language, and proposing evidence-based responses. Using the Watson™ services, a physician can submit a particular patient's healthcare data 114, wherein the Watson™ services analyze the patient's healthcare data 114 using the machine learning models 112, and offers feedback to the physician regarding the diagnoses of the patient's health.

However, there are problems in tracking usage of machine learning models 112 and healthcare data 114 as assets. When accessed as a service, it is difficult to track model 112 dependencies. When generated by healthcare data 114 from different sources, it is difficult to track which healthcare data 114 accurately trained the models 112. When the service is based on interdependent models 112, it is difficult to track which model 112 provides the most accurate results.

Hyperledger Fabric

In one embodiment of the present invention, the machine learning models 112 are shared and utilized using a blockchain 118 as a distributed ledger that is shared, replicated and synchronized by the hyperledger fabric 106, wherein the blockchain records transactions involving the machine learning models 112. A blockchain is a continuously growing list of records, called blocks, which are linked and secured using cryptography. Blocks store one or more items of data, such as transactions involving the machine learning models 112, that are hashed and encoded.

The blockchain 118 records access to and usage of the machine learning models 112, as well as records transactions for owners of the models 112, such as transfers of rights to use the models 112 from other owners. In addition, the blockchain 118 tracks dependencies among the models 112; the blockchain 118 tracks services built upon the models 112; the blockchain 118 provides for selection among the models 112; and the blockchain 118 ensures that access to the models 112 is in compliance with regulatory requirements. Moreover, the blockchain 118 includes at least one uniform resource locator (URL) that provides access to the models 112 that is added as a configuration to the cognitive computing services 104.

In this embodiment, the hyperledger fabric 106 uses smart contracts 120, also known as chaincodes, to control access to the blockchain 118 and machine learning models 112. A smart contract 120 is a computer-implemented protocol to facilitate, verify or enforce negotiation or performance of the transactions involving the healthcare-derived resources.

A smart contract 120 makes billing transparent with regards to the machine learning models 112. Using the smart contract 120, the hyperledger fabric 106 validates and orders transactions associated with the machine learning models 112 in the blockchain 118. Moreover, access to the machine learning models 112 and healthcare data 114 can be enabled or disabled according to a service level agreement (SLA) embodied in the smart contract 120.

In this embodiment, smart contracts 120 are written to allow participants to execute certain aspects of transactions automatically. A smart contract 120 can, for example, be written to stipulate the cost of accessing the machine learning model 112. With the terms agreed to by both parties and written to the blockchain 118, the appropriate funds are exchanged automatically when the machine learning model 112 is accessed.

The hyperledger fabric 106, being a permissioned platform, enables confidentiality through its channel architecture. Basically, a "channel" can be established between a subset of participants that are granted visibility to a particular set of transactions. Thus, only those participants in the channel have access to the smart contract 120 and associated transactions, preserving the privacy and confidentiality of both.

Configuration System

In one embodiment of the present invention, the configuration system 108 works with the hyperledger fabric 106 to configure, administer and authorize both the cognitive computing services 104 and the app 116. Specifically, the configuration system 108 configures the machine learning model 112 and healthcare data 114, administers their operations, and authorizes the app 116 to communicate with the associated insights service of the cognitive computing services 104. For example, the configuration system 108 configures the cognitive computing services 104, where the machine learning models 112 may be "pluggable" or dynamically loaded into the cognitive computing services 104. The configuration system 108 also obtains the URL of the insights service that is used to access machine learning model 112 from the hyperledger fabric 106, and provides that URL to the app 116 on the client computer device 110A, 110B.

Use Cases

A number of use cases provide examples where sharing machine learning models 112 and healthcare data 114 can further healthcare research and help treat patients. For example, many problems in healthcare can be formulated as learning problems. If a healthcare problem can be formulated as a machine learning problem, and if there exists an entity with enough data 114 to identify patterns that correctly solve this problem, then providing an infrastructure to share machine learning models 112 will greatly benefit healthcare organizations which lack healthcare data 114, while incentivizing the creation and sharing of machine learning models 112 by healthcare organizations which have healthcare data 114.

Accessing a Machine Learning Model

In this use case, an end-user, such as a doctor, executes an app 116 on a client computing device 110A, 110B, wherein the app 116 is used to access the insights service of the cognitive computing services 104 associated with one or more machine learning models 112 that may be selected by the end-user. The app 116 communicates a request to use a selected one of the machine learning models 112 to the hyperledger fabric 106.

The hyperledger fabric 106 receives the request, and accesses the associated smart contract 120 to determine whether to grant access to the machine learning model 112. If access is granted, the hyperledger fabric 106 uses the blockchain 118 to settle payment for use of the machine learning model 112 and adds a transaction record to the blockchain 118.

The hyperledger fabric 106 communicates this grant of access to the configuration system 108, along with the URL of the insights service of the cognitive computing services 104 hosting the machine learning model 112. The configuration system 108 communicates with the cognitive computing services 104 to configure the machine learning model 112.

The configuration system 108 also supplies the URL to the app 116, and activates the app 116 on the client computing device 110A, 110B (e.g., by activating a request button in the app 116). When the app 116 accesses the URL, a user interface for the insights service may display the accuracy, cost, and other metadata or other information for the machine learning models 112.

When invoked, the app 116 transmits data 114 from the client computing device 110A, 110B to the insights service of the cognitive computing services 104. The data 114 may include text, images, video, audio or any data that requires analysis, classification, prediction or insight. The cognitive computing services 104 then invokes the machine learning model 112, which analyzes the data 114. The results of the analysis are then returned to the app 116 on the client computing devices 110A, 110B for review by the end-user.

Diagnosis using a Machine Learning Model

In this use case, a patient visits a doctor at a clinic, where the doctor has the patient's history stored in an Electronic Medical Record (EMR). The EMR indicates that the patient has made multiple clinic visits for different chronic conditions recently. Moreover, the patient complains about heart pain and eats lot of sugar.

The doctor needs a tool that will analyze and classify these symptoms, for instance, about the patient's heart condition or the patient's chances of some other diseases. The doctor accesses one or more of the machine learning models 112 supported by the insights service of the cognitive computing services 104, as described above.

The doctor determines that a heart disease machine learning model 112 from hospital A and a cancer machine learning model 112 from hospital Z are accurate. The accuracy of these machine learning models 112 can be determined by metadata stored with the data 114 associated with the machine learning models 112, which may be displayed on the user interface for the insights service. Moreover, the metadata may be used to select among the models 112 and data 114, wherein the metadata can include, but is not limited to, metrics like accuracy, precision and recall.

When a doctor selects a machine learning model 112, an accuracy score from the metadata may be displayed as High, Medium or Low. The selection results in a request with the patient data 114 being sent to the insights service for analysis of the patient data 114 by the machine learning model 112. The doctor then waits for some period of time for the results of the analysis to be returned, and then the doctor uses the results in an appropriate way to help to treat the patient.

The charges to use the machine learning models 112 from hospital A and hospital Z are settled through smart contracts 120 in the blockchain 118. For example, the patient's insurance company may be directly charged for use of the machine learning models 112 in a transparent manner. In another example, if the machine learning models 112 from both hospitals A and Z are involved, then the billing can be split between the hospitals, such as in a barter system, where hospital A leases its machine learning model 112 to hospital B, or vice versa, which could be useful for research or beta testing. These details can be made part of the smart contract 120.

Detecting Hard-to-Diagnosis Conditions Using a Machine Learning Model

This use case concerns hard-to-detect conditions, for example, diabetic retinopathy (DR). Currently, detecting diabetic retinopathy is a time-consuming and manual process that requires a trained clinician to examine and evaluate digital color fundus photographs of the retina, wherein diabetic retinopathy can be identified by the presence of lesions associated with the vascular abnormalities caused by the disease. By the time a clinician submits their reviews, often a day or two later, the delayed results may lead to lost follow up, miscommunication, and delayed treatment.

While the current approach is effective, its resource demands are high. The expertise and equipment required are often lacking in many geographic areas where the rate of diabetes in local populations is high and detection of diabetic retinopathy is most needed. As the number of individuals with diabetes continues to grow, the infrastructure needed to prevent blindness due to diabetic retinopathy will become even more insufficient.

In this invention, however, the doctor may access one or more of the machine learning models 112 supported by services like the insights service of the cognitive computing services 104, as described above. These machine learning models 112 may be accurate in analyzing data 114 comprised of digital color fundus photographs of the retina uploaded to the insights service, and identifying diabetic retinopathy by the presence of lesions in those photographs. Moreover, these machine learning models 112 likely can perform the analysis and return results of the analysis in a short amount of time. Again, the charges to use these machine learning models 112 are settled through smart contracts 120 in the blockchain 118.

Adding a Machine Learning Model to the Cognitive Computing Services

In this use case, a machine learning model 112 is added to the cognitive computing services 104. Using the app 116, the owner of the machine learning model 112 communicates with the hyperledger fabric 106 to obtain a URL for the machine learning model 112. The URL points to an insights service of the cognitive computing services 104 that will deploy the machine learning model 112.

The hyperledger fabric 106 adds the URL to a smart contract 120 for the machine learning model 112. The smart contract 120 provides specifications for use of the machine learning model 112, such as who may use the machine learning model 112, billing for usage, split revenues for owner or other service providers resulting from collaboration, barter between the owner and other service providers, etc.

Pluggable Machine Learning Models

This use case concerns "pluggable" machine learning models 112. Specifically, the configuration system 108 may dynamically load machine learning models 112 into the insights service of the cognitive computing services 104. Different machine learning models 112 can be generated from different data 114 provided by different entities, and the machine learning models 112 may differ in terms of accuracy, size, precision or any other metric. The machine learning models 112 may be dynamically loaded in response end-user requests, based on some qualifying condition like accuracy, size, precision or any other metric. Moreover, new machine learning models 112 may be dynamically loaded when added to the system.

Reuse of a Machine Learning Model

This use case concerns reuse of a machine learning model 112, which is a resource owned by an entity. A resource owned by an entity A can be shared with entity B, and entity B can reuse this resource to create a new resource with the data from entity B.

Consider an example after a machine learning model 112 for a particular type of cancer has been provisioned for service, wherein the machine learning model 112 is owned by a first entity. In this example, a second entity requests access to the machine learning model 112, and such access is permitted by the smart contract 120.

The hyperledger fabric 106 generates a new URL for the insights service used by the second entity. From this new URL, the machine learning model 112 is plugged into the insights service, so that the machine learning model 112 can be accessed via the insights service remotely. Moreover, the machine learning model 112 accessed by the new URL may be re-configured using data 114 from the second entity.

In the above case, each access to the machine learning model 112 via the new URL is logged into the blockchain 118 using the same or a different smart contract 120, which makes billing transparent.

Barter of Machine Learning Models

This use case concerns barter of machine learning models 112. Consider an example where a first entity has cancer data and a second entity has hernia data. Assume that a first machine learning model 112 for the cancer data has been provisioned for service, wherein the first machine learning model 112 is owned by the first entity. Assume that a second machine learning model 112 for the hernia data has been provisioned for service, wherein the second machine learning model 112 is owned by the second entity. In this example, the first and second entities may enter into a barter agreement to offer usage of each other's machine learning model 112. The barter agreement can be defined within a smart contract 120.

Sharing a Machine Learning Model

This use case concerns sharing of a machine learning model 112. Consider an example where different types of end-users, such as doctors and researchers, want to access different kinds of machine learning models 112 for "walk-in" patients (a doctor) or for performing research (a researcher).

In such a scenario, depending on the access, the doctor or researcher could select the desired machine learning models 112 to perform an analysis of data 114. The usage and the billing are controlled by the smart contracts 120 associated with the desired machine learning models 112.

In this example, multiple producers and consumers of the machine learning models 112 and data 114 are willing to share the machine learning models 112 and data 114.

Leasing a Machine Learning Model

In this use case, machine learning models 112 are leased to the insights service of the cognitive computing services 104. The terms of the lease are determined by the associated smart contract 120.

Subleasing a Machine Learning Model

In this use case, machine learning models 112 are sub-leased by an owner to another entity. The sub-lease may allow a new version of the machine learning model 112 to be trained using data 114 provided by the sub-leasing entity. The terms of the sub-lease are determined by the associated smart contract 120.

Transferring Rights to a Machine Learning Model

This use case concerns transferring rights to a machine learning model 112 or data 114. The rights to a machine learning model 112 can be transferred from one entity to another through a custom data structure stored in the blockchain 118, called a Right Transfer Transaction (RTT). Each RTT must contain a (direct or indirect) link to the smart contract 120 whose rights are being exchanged.

When transferring its right through an RTT, an owner can modify the mutable conditions regulating its right only by restricting them. For instance, supposing that a changeable condition defined by the resource owner (or by the previous right owner) states the access can be performed from 9.00 AM to 5.00 PM, the owner could transfer this right to another entity by restricting the access time from 9.00 AM to 1.00 PM. The owner can also split its right in two (or more) parts, and transfer one part to one entity, and can transfer another part to another entity. With reference to the previous example, the owner could transfer the access right from 1.00 PM to 5.00 PM to yet another entity.

It is noted that the owners are only owners of rights to perform actions; in general, the owners have no other right concerning either policy or resources. It is also remarked that owners are able to freely exchange action rights between themselves without any interaction with a policy issuer. That implies that the policy issuer (in general, corresponding to the resource owner) has no knowledge in advance of which entities will be the policy right beneficiaries (even if it can of course model a subject prototype by specifying the correct attributes conditions to be satisfied inside the policy).

It is also noted that policy updates from a resource owner can potentially change the meaning of a policy. This means that subjects can gain rights on a certain resource that can be later changed by the policy issuer, but, since the blockchain 118 never forgets and timestamps both the rights transfer and the policy updates, those changes are manifest and traceable.

Advantages and Benefits

The present invention includes a number of advantages:

This invention also provides a simple means for selection of machine learning models 112.

This invention provides a trustful, auditable framework for collaboration between various healthcare providers.

This invention also provides a transparent way to determine the usage of value-added services used by the hospitals.

One benefit of this invention concerns privacy. Using a permissioned blockchain allows only entities who have rights to view the transactions. A permissionless blockchain is ideal as a shared database where everyone can read everything, but no single user controls who can write. In this invention, transactions are visible only to those entities with access rights.

Another benefit of this invention concerns scalability. A permissioned blockchain can build a simplified proof-of-stake model to establish consensus, which eliminates the need for proof-of-work computations. The ultimate result is scalability as compared to a public permissionless blockchain network.

Yet another benefit of this invention concerns fine-grained access control. A permissioned blockchain allows only restricted access to the transaction within the ledger.

Flowchart

Figure 2:
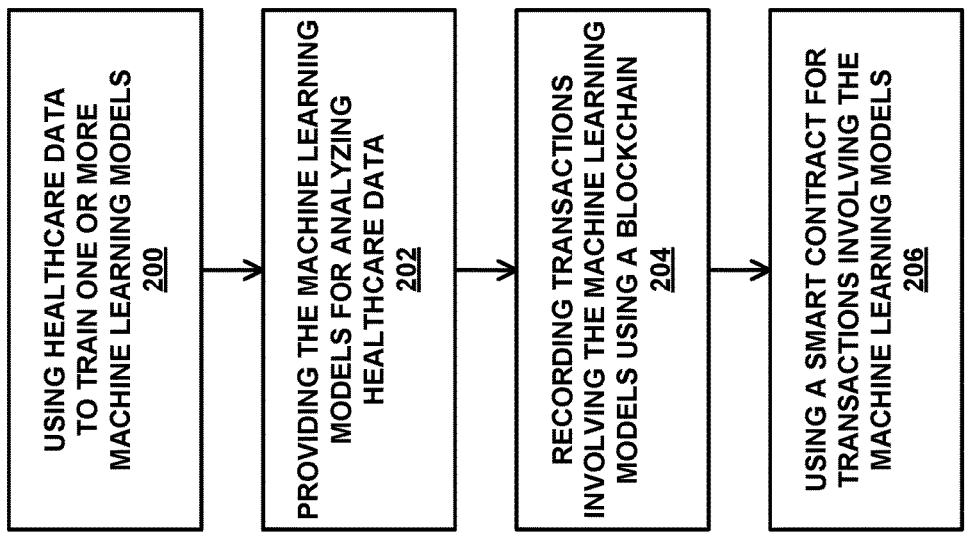
FIG. 2 illustrates an exemplary method for sharing and utilizing healthcare-derived resources according to an embodiment of the present invention.

FIG. 2 illustrates an exemplary method for sharing and utilizing healthcare data, according to an embodiment of the present invention.

Block 200 represents the cognitive computing services 104 using healthcare data 114 to train one or more computer-implemented machine learning models 112, wherein the healthcare data 114 comprises research data or patient data.

Block 202 represents the cognitive computing services 104 providing the computer-implemented machine learning models 112 for analyzing healthcare data 114.

Block 204 represents the hyperledger fabric 106 recording transactions involving the machine learning models 112 using a blockchain 118 as a distributed ledger that is shared, replicated and synchronized.

The blockchain 118 records access to and usage of the machine learning models 112 and healthcare data 114. The blockchain 118 also tracks dependencies among the machine learning models 112 and healthcare data 114. In addition, the blockchain 118 tracks services built upon the machine learning models 112 and healthcare data 114.

The blockchain 118 includes at least one uniform resource locator (URL) that provides access to the machine learning models 112 and healthcare data 114 that is delivered as a service. The blockchain 118 also provides for selection among the machine learning models 112, wherein metadata is used to select among the machine learning models 112.

The blockchain 118 ensures that access to the healthcare data 114 is in compliance with regulatory requirements.

The blockchain also records transactions between owners of the machine learning models 112 and healthcare data 114, for example, the blockchain 118 may be used to transfer rights to use the machine learning models 112.

Block 206 further comprises using a smart contract that is a computer-implemented protocol to facilitate, verify or enforce negotiation of the transactions involving the machine learning models 112 and healthcare data 114.

Cloud Computing

It is to be understood that, although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3:
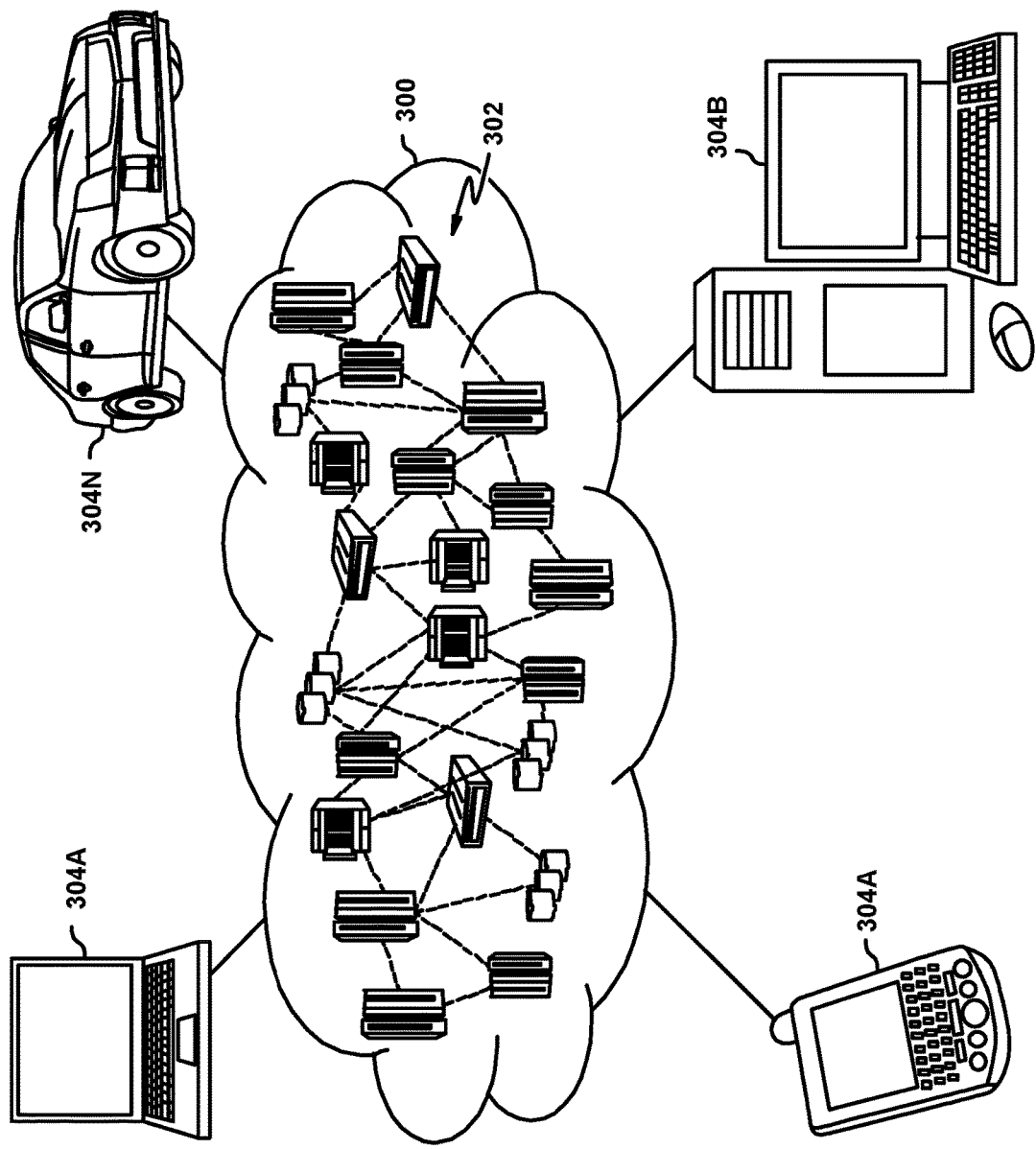
FIG. 3 depicts a cloud computing environment according to an embodiment of the present invention.

Referring now to FIG. 3, an illustrative cloud computing environment 300 is depicted. As shown, cloud computing environment 300 includes one or more cloud computing nodes 302 with which local computing devices used by cloud consumers, such as, for example, personal digital assistant (PDA) or cellular telephone 304A, desktop computer 304B, laptop computer 304C, and/or automobile computer system 304N may communicate. Nodes 302 may communicate with one another. They may be grouped (not shown) physically or virtually, in one or more networks, such as Private, Community, Public, or Hybrid clouds as described hereinabove, or a combination thereof. This allows cloud computing environment 10 to offer infrastructure, platforms and/or software as services for which a cloud consumer does not need to maintain resources on a local computing device. It is understood that the types of computing devices 304A-N shown in FIG. 3 are intended to be illustrative only and that computing nodes 302 and cloud computing environment 300 can communicate with any type of computerized device over any type of network and/or network addressable connection (e.g., using a web browser).

Figure 4:
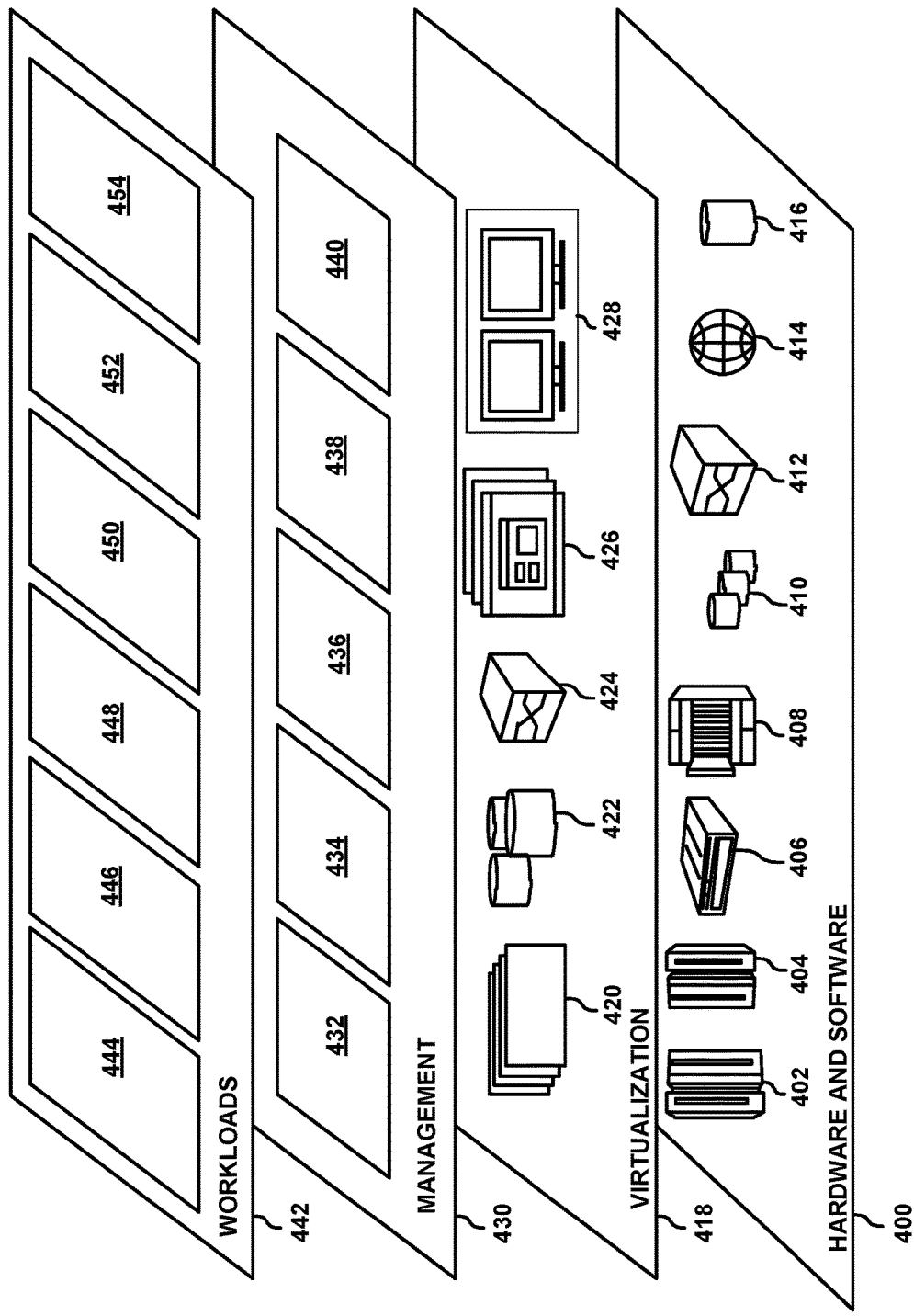
FIG. 4 depicts abstraction model layers according to an embodiment of the present invention.

Referring now to FIG. 4, a set of functional abstraction layers provided by a cloud computing environment is shown. It should be understood in advance that the components, layers, and functions shown in FIG. 4 are intended to be illustrative only and embodiments of the invention are not limited thereto. As depicted, the following layers and corresponding functions are provided:

Hardware and software layer 400 includes hardware and software components. Examples of hardware components include: one or more computers such as mainframes 402; RISC (Reduced Instruction Set Computer) architecture based servers 404; servers 406; and blade servers 408; storage devices 410; and networks and networking components 412. In some embodiments, software components include network application server software 414 and database software 416.

Virtualization layer 418 provides an abstraction layer from which the following examples of virtual entities may be provided: virtual servers 420; virtual storage 422; virtual networks 424, including virtual private networks; virtual applications and operating systems 426; and virtual clients 428.

In one example, management layer 430 may provide the functions described below. Resource provisioning 432 provides dynamic procurement of computing resources and other resources that are utilized to perform tasks within the cloud computing environment. Metering and pricing 434 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 436 provides access to the cloud computing environment for consumers and system administrators. Service level management 438, which includes containers, provides cloud computing resource allocation and management such that required service levels are met. Service Level Agreement (SLA) planning and fulfillment 440 provide pre-arrangement for, and procurement of, cloud computing resources for which a future requirement is anticipated in accordance with an SLA.

Workloads layer 442 provides examples of functionality for which the cloud computing environment may be utilized. Examples of workloads, tasks and functions which may be provided from this layer include: data collection 444, machine learning 446, transaction processing 448; blockchain processing 450; operations management 452; audit control 454; etc.

Computer Program Product

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to illustrations and/or block diagrams of methods, apparatus (systems), and computer program products according to embodiments of the invention. It will be understood that each block of the illustrations and/or block diagrams, and combinations of blocks in the illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the illustrations and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the illustrations and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the illustrations and/or block diagram block or blocks.

The illustrations and block diagrams in the Figures illustrate the architecture, functionality, and operation of possible implementations of systems, methods, and computer program products according to various embodiments of the present invention. In this regard, each block in the illustrations or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or illustrations, and combinations of blocks in the block diagrams and/or illustrations, can be implemented by special purpose hardware-based systems that perform the specified functions or acts or carry out combinations of special purpose hardware and computer instructions.

CONCLUSION

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
    collecting, by a computer, healthcare data comprising research data and historical patient data from electronic medical records;
    training, by the computer, one or more computer-implemented machine learning models using the collected healthcare data using cognitive computer services for performing an analysis of the research data and the historical patient data to recognize patterns and generate diagnoses of the historical patient data based on the recognized patterns, wherein each model of the one or more computer-implemented machine learning models is trained on a subset of the collected healthcare data comprising a single category of illness;
    determining, by the computer, an accuracy of each model by comparing generated diagnoses of the historical patient data of each model diagnoses in related metadata stored with the healthcare data;
    providing, by the computer, an accuracy score to a physician of each model for the corresponding single category of illness, wherein the accuracy score is selected from a group consisting of high, medium and low;
    receiving, by the computer, from the physician a selection of one model and a first patient's healthcare data;
    ensuring, by the computer, that physician access to healthcare data is in compliance with regulatory requirements by recording transactions between owners of each model and owners of the healthcare data, and by recording transfer rights to use each model by tracking dependencies using a blockchain as a distributed ledger which is shared, replicated and synchronized;

providing, by the computer, the one or more computer-implemented machine learning models for analyzing the healthcare data, wherein providing the one or more computer-implemented machine learning models comprises:

using cognitive computing services for analyzing the first patient's healthcare data with the model selected by the physician; and providing, by the computer, a first diagnosis of the first patient's healthcare data from the selected model to the physician;

after providing the first diagnosis of the first patient's data, recording, by the computer, physician usage of transactions involving the selected model and the first diagnosis using the blockchain as a distributed ledger that is shared, replicated and synchronized; and transferring funds, by the computer, to settle payment by the physician for the physician usage, based on a previously agreed to smart contract, wherein the smart contract is a computer-implemented protocol to facilitate and verify performance of transactions involving use of the trained set of computer-implemented machine learning models.

2. The method of claim 1, further comprising: tracking, by the computer, a subset of healthcare data used by each of the one or more computer-implemented machine learning models and a source of the subset of healthcare data used, using the blockchain.

3. The method of claim 1, wherein the blockchain records access to and usage of the machine learning models or healthcare data.

4. The method of claim 1, wherein the blockchain tracks dependencies among the machine learning models or healthcare data.

5. The method of claim 1, wherein the blockchain tracks services built upon the machine learning models or healthcare data.

6. The method of claim 1, wherein the blockchain includes at least one uniform resource locator (URL) that provides access to the machine learning models or healthcare data that are delivered as a service.

7. The method of claim 1, wherein the blockchain provides for selection among the machine learning models.

8. The method of claim 1, wherein the blockchain records transactions between owners of the machine learning models or healthcare data.

9. The method of claim 1, wherein the blockchain transfers rights to use the machine learning models or healthcare data.

10. A computer-implemented system, comprising:

one or more computers programmed for sharing and utilizing healthcare data, one or more computer-readable storage media, and program instructions stored on the one or more of the computer-readable storage media for execution by at least one of the one or more processors, the program instructions executable by a computing system to cause the computing system to perform a method comprising:

collecting healthcare data comprising research data and historical patient data from electronic medical records;

training the one or more computer-implemented machine learning models using the collected healthcare data using cognitive computer services for performing an analysis of the research data and the historical patient data to recognize patterns and generate diagnoses of the historical patient data based on the recognized patterns, wherein each model of the trained set of computer-implemented machine learning models is trained on a subset of the collected healthcare data comprising a single category of illness;

determining an accuracy of each model by comparing generated diagnoses of the historical patient data of each model diagnoses in related metadata stored with the healthcare data:

providing an accuracy score to a physician of each model for the corresponding single category of illness, wherein the accuracy score is selected from a group consisting of high, medium and low;

receiving from the physician a selection of one model and a first patient's healthcare data;

ensuring that the physician access to the healthcare data is in compliance with regulatory requirements by recording transactions between owners of each model and owners of the healthcare data, and by recording transfer rights to use each model by tracking dependencies using a blockchain as a distributed ledger which is shared, replicated and synchronized;

providing the one or more computer-implemented machine learning models for analyzing the healthcare data, wherein providing the one or more computer-implemented machine learning models comprises:

using cognitive computing services for analyzing the first patient's healthcare data with the model selected by the physician; and providing a first diagnosis of the first patient's healthcare data from the selected model to the physician;

after providing the first diagnosis of the first patient's data, recording physician usage of transactions involving the selected model and the first diagnosis using the blockchain as a distributed ledger that is shared, replicated and synchronized; and transferring funds to settle payment by the physician for the physician usage, based on a previously agreed to smart contract, wherein the smart contract is a computer-implemented protocol to facilitate and verify performance of transactions involving use of the trained set of computer-implemented machine learning models.

11. The system of claim 10, further comprising:

tracking a subset of healthcare data used by each of the one or more computer-implemented machine learning models and a source of the subset of healthcare data used, using the blockchain.

12. The system of claim 10, wherein:

the blockchain records access to and usage of the machine learning models or healthcare data;

the blockchain tracks dependencies among the machine learning models or healthcare data; and the blockchain tracks services built upon the machine learning models or healthcare data.

13. The system of claim 10, wherein the blockchain includes at least one uniform resource locator (URL) that provides access to the machine learning models or healthcare data that are delivered as a service, and the blockchain provides for selection among the machine learning models, wherein the metadata is used to select among the machine learning models.

14. The system of claim 10, wherein the blockchain ensures that access to the healthcare data is in compliance with regulatory requirements, the blockchain records transactions between owners of the machine learning models or healthcare data, and the blockchain transfers rights to use the machine learning models.

15. A computer program product, the computer program product comprising a computer readable storage medium having program instructions embodied therewith, the program instructions executable by one or more computers to cause the computers to perform a method comprising:
    collecting healthcare data comprising research data and historical patient data from electronic medical records;
    training the one or more computer-implemented machine learning models using the collected healthcare data using cognitive computer services for performing an analysis of the research data and the historical patient data to recognize patterns and generate diagnoses of the historical patient data based on the recognized patterns, wherein each model of the trained set of computer-implemented machine learning models is trained on a subset of the collected healthcare data comprising a single category of illness;
    determining an accuracy of each model by comparing generated diagnoses of the historical patient data of each model diagnoses in related metadata stored with the healthcare data;
    providing an accuracy score to a physician of each model for the corresponding single category of illness, wherein the accuracy score is selected from a group consisting of high, medium and low;
    receiving from the physician a selection of one model and a first patient's healthcare data;
    ensuring that the physician access to the healthcare data is in compliance with regulatory requirements by recording transactions between owners of each model and owners of the healthcare data, and by recording transfer rights to use each model by tracking dependencies using a blockchain as a distributed ledger which is shared, replicated and synchronized;
    providing the one or more computer-implemented machine learning models for analyzing the healthcare data, wherein providing the one or more computer-implemented machine learning models comprises:
    providing an accuracy score to a physician of each model for the corresponding single category of illness, wherein the accuracy score is selected from a group consisting of high, medium and low;
    receiving from the physician a selection of one model and a first patient' 5 hcalthcarc data;
    using cognitive computing services for analyzing the first patient's healthcare data with the model selected by the physician; and
    providing a first diagnosis of the first patient's healthcare data from the selected model to the physician;
    after providing the first diagnosis of the first patient's data, recording physician usage of transactions involving the selected model and the first diagnosis using the blockchain as a distributed ledger that is shared, replicated and synchronized; and
    transferring funds to settle payment by the physician for the physician usage, based on a previously agreed to smart contract, wherein the smart contract is a computer-implemented protocol to facilitate and verify performance of transactions involving use of the trained set of computer-implemented machine learning models.

16. The computer program product of claim 15, further comprising:
    tracking a subset of healthcare data used by each of the one or more computer-implemented machine learning models and a source of the subset of healthcare data used, using the blockchain.

17. The computer program product of claim 15, wherein:
    the blockchain records access to and usage of the machine learning models or healthcare data;
    the blockchain tracks dependencies among the machine learning models or healthcare data; and
    the blockchain tracks services built upon the machine learning models or healthcare data.

18. The computer program product of claim 15, wherein the blockchain includes at least one uniform resource locator (URL) that provides access to the machine learning models or healthcare data that are delivered as a service, and the blockchain provides for selection among the machine learning models, wherein the metadata is used to select among the machine learning models.

19. The computer program product of claim 15, wherein the blockchain ensures that access to the healthcare data is in compliance with regulatory requirements, the blockchain records transactions between owners of the machine learning models or healthcare data, and the blockchain transfers rights to use the machine learning models.

* * * * *